(12) United States Patent
Takeno et al.

(10) Patent No.: US 8,018,239 B2
(45) Date of Patent: Sep. 13, 2011

(54) METHOD AND DEVICE FOR MEASURING POWDER PROPERTIES

(75) Inventors: Mitsuhiro Takeno, Osaka (JP); Kazuhiro Okamura, Osaka (JP)

(73) Assignee: Panasonic Corporation, Osaka (JP)

( * ) Notice: Subject to any disclaimer, the term of this patent is extended or adjusted under 35 U.S.C. 154(b) by 292 days.

(21) Appl. No.: 12/403,702

(22) Filed: Mar. 13, 2009

(65) Prior Publication Data
US 2009/0237095 A1 Sep. 24, 2009

(30) Foreign Application Priority Data

Mar. 18, 2008 (JP) ................................ 2008-069959

(51) Int. Cl.
*G01R 27/08* (2006.01)
(52) U.S. Cl. ...................................................... 324/693
(58) Field of Classification Search .......... 324/691–713
See application file for complete search history.

(56) References Cited

U.S. PATENT DOCUMENTS

| | | | | |
|---|---|---|---|---|
| 5,442,298 A * | 8/1995 | Chang | ............................ | 324/724 |
| 5,864,239 A * | 1/1999 | Adams et al. | ................. | 324/636 |
| 6,218,846 B1 * | 4/2001 | Ludwig et al. | ................ | 324/713 |
| 6,300,123 B1 * | 10/2001 | Vadgama et al. | ........... | 435/287.1 |
| 7,199,591 B2 * | 4/2007 | Ehata | ............................ | 324/636 |
| 7,609,073 B2 * | 10/2009 | Olson et al. | .................... | 324/691 |
| 7,696,763 B1 * | 4/2010 | Sun | ................................. | 324/707 |
| 7,821,269 B2 * | 10/2010 | Petrovsky et al. | ............ | 324/341 |
| 2007/0268027 A1 * | 11/2007 | Olsen et al. | .................. | 324/691 |

OTHER PUBLICATIONS

"Correct Measurement and Evaluation of Electrical Characteristics," Technical Information Institute Co., Ltd., and NPC, pp. 130-131, 2005, with partial English Translation.

\* cited by examiner

*Primary Examiner* — Huy Q Phan
*Assistant Examiner* — Joshua Benitez
(74) *Attorney, Agent, or Firm* — McDermott Will & Emery LLP

(57) ABSTRACT

An object of the present invention is to provide a method for measuring information relating to the impedance characteristics of a powder with high accuracy. To achieve such an object, the method for measuring powder properties according to the present invention includes a step in which the impedance characteristics of a powder are obtained by an alternating current impedance method, using a function setting a pressure applied to the powder or a density of the powder as a variable. From the obtained impedance characteristics, information relating to at least one of the components can be extracted, the components being a first component that is dependent on the variable, and a second component that is not dependent on the variable.

6 Claims, 4 Drawing Sheets

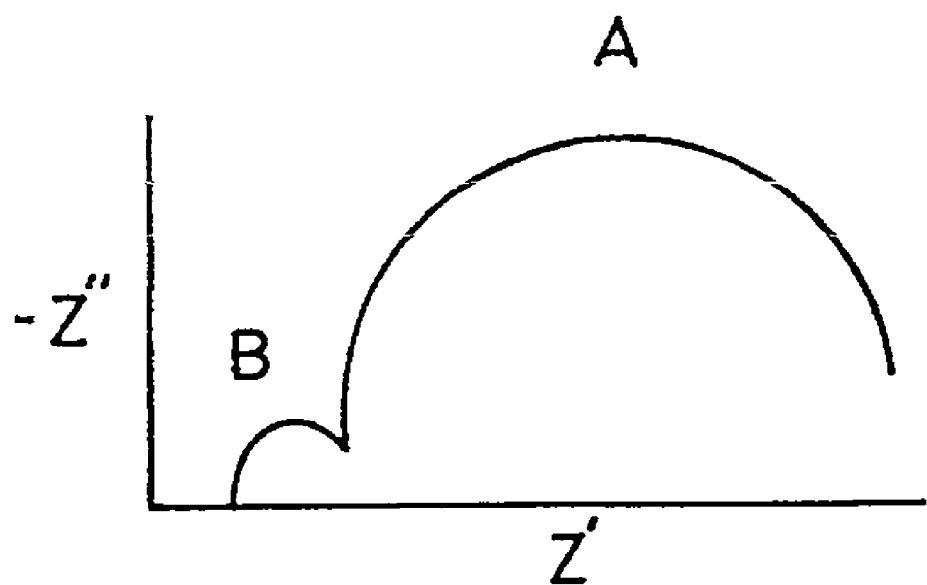
F I G. 1

METHOD AND DEVICE FOR MEASURING POWDER PROPERTIES

FIELD OF THE INVENTION

The present invention relates to a method and a device for measuring powder properties, in which information relating to powder properties, especially information relating to the impedance characteristics of a powder can be measured with high accuracy.

BACKGROUND OF THE INVENTION

With the advancement of science and technology, improvements in product productivity and the quality control of materials have recently been considered important. In view of such considerations, the measurement of material properties is very important, and various measurement methods for properties such as the impedance, resistance, and density of materials have been examined. For example, the four probe method (JIS K $7194_{-1994}$; Testing Method for Resistivity of Conductive Plastics with a Four-Point Probe Array) has been known as a method for measuring the resistance of a material. In the four probe method, four needlelike probes (electrodes) arranged in substantially a line are brought into contact with a test piece, and the resistivity of the test piece is obtained from a direct current applied between the outer two probes and the potential difference between the inner two probes. Note that the measurement method described in JIS K 7194 is a method for measuring the resistivity of a plate-like test piece, and does not relate to a method for measuring the resistance of a powder.

A direct current is generally used for measuring the resistance of a powder. "Correct Measurement and Evaluation of Electrical Characteristics" (Technical Information Institute Co., Ltd, and NPC, pp. 130 to 131 (2005)) describes a method for measuring the powder resistivity of carbon nanotubes (CNT). In this measurement method, a predetermined amount of CNT is packed into a measurement cell and a pressure is applied thereon in stages to evaluate the behavior of the powder under certain CNT densities. Then, the direct-current resistance of CNT is measured while changing the density of the powder.

In measurements using a direct current, however, the resistance component between particles and the resistance component inside particles cannot be separated. Thus, there is limitation in the amount of information obtained regarding powder properties. Also, there are disadvantages in that because a direct current resistance is measured based on Ohm's law, the resistance changes due to Joule heating, and the measurement value is not stable.

On the other hand, measuring the resistance of powder by an alternating current impedance method has also been proposed. In this case, generally, powder is sintered or pressed in advance to form a molded product therefrom, and the resistance is measured. By using the molded product for the measurement, variation in measurement values due to changes in powder density can be prevented.

In the above case, however, because the molded product is used for the measurement, no discussion can be made regarding the relationship between density and resistance. Furthermore, because of the poor reproducibility of the measurement values, it is difficult to obtain highly reliable measurement results.

BRIEF SUMMARY OF THE INVENTION

An object of the present invention is to measure information relating to powder properties, particularly, information relating to the impedance characteristics of a powder with high accuracy.

A method for measuring powder properties according to the present invention includes step A in which impedance characteristics of a powder are obtained by an alternating current impedance method as a function of a variable, said variable being a pressure applied to the powder or a density of the powder.

A preferable embodiment of the method for measuring powder properties according to the present invention further includes step B in which information relating to at least one of the components is extracted from the obtained impedance characteristics, the components being a first component that is dependent on the variable, and a second component that is not dependent on the variable.

A preferable embodiment of the method for measuring powder properties according to the present invention further includes at least one of step C in which information relating to the resistance between the particles of powder is obtained from the first component, and step D in which information relating to the resistance inside the particles of powder is obtained from the second component.

In an embodiment of the present invention, step A includes changing the frequency of the alternating current or the alternating voltage while fixing a variable (the pressure applied to a powder or the density of a powder) at a predetermined value Xn, and obtaining the relationships between the frequency and the impedance of a powder at a predetermined value Xn.

In an embodiment of the present invention, step A includes successively changing a variable (the pressure applied to a powder or the density of a powder) while fixing the frequency of the alternating current or the alternating voltage at a predetermined value Ym, and obtaining the relationships between the variable and the impedance of the powder at the predetermined value Ym.

In the method for measuring powder properties according to the present invention, the pressure applied to a powder or the density of a powder is preferably changed by applying a pressure to the powder in one direction in a space surrounded by a conductive material, and successively increasing the pressure.

The present invention also relates to a device for measuring powder properties, the device including: a measurement container forming a space surrounded by a conductive material that is grounded; a pressing apparatus that presses powder packed in the measurement container; a pair of current terminals and a pair of voltage terminals that are exposed inside the measurement container; a power source that applies an alternating current of an arbitrary frequency to the pair of current terminals, or an alternating voltage of an arbitrary frequency to the pair of voltage terminals, while the pressing apparatus is applying a pressure to the powder; an analysis device that analyzes a voltage generated between the pair of voltage terminals by the application of the alternating current or an electric current generated between the pair of current terminals by the application of the alternating voltage; and a calculator that calculates the impedance of the powder from the voltage generated between the pair of voltage terminals or the electric current generated between the pair of current terminals.

In the device for measuring powder properties according to the present invention, a characteristic impedance of the pair of current terminals, a characteristic impedance of the pair of voltage terminals, and a characteristic impedance of the power source are preferably matched.

According to the method for measuring powder properties of the present invention, the resistance component inside the particles, and the resistance component between the particles can be separated with high accuracy. Therefore, information relating to the impedance characteristics of a powder can be measured highly accurately.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 1 is a complex impedance plot illustrating an example of the impedance characteristics that are obtained in step A according to the present invention.

DETAILED DESCRIPTION OF THE INVENTION

Figure 2:
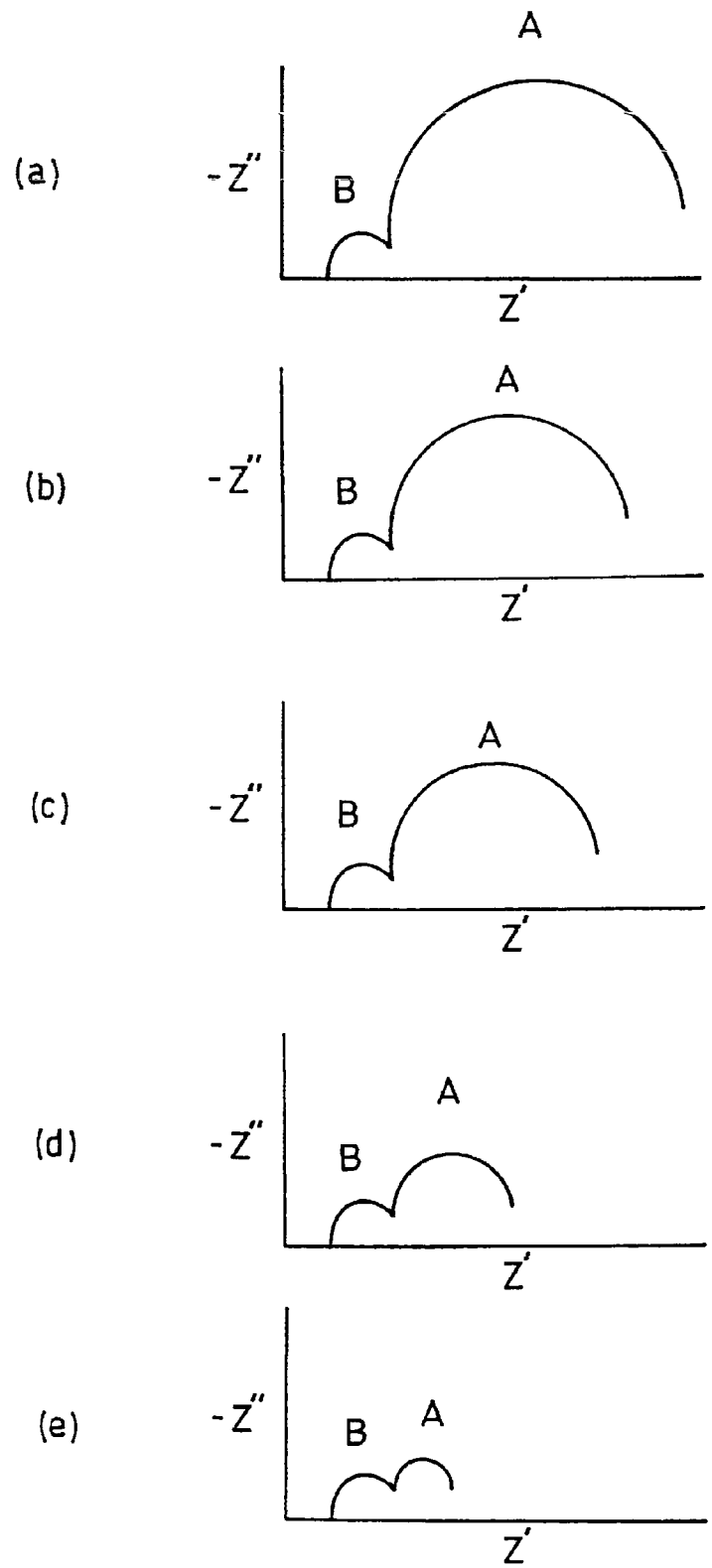
FIG. 2 shows examples of a plurality of complex impedance plots that are obtained by changing the variable to X1 to X5.

The present invention provides a method for measuring powder properties relating to the impedance characteristics of a powder. The measurement method of the present invention includes step A in which the impedance characteristics of a powder are obtained by an alternating current impedance method as a function of a variable, said variable being a pressure applied to the powder or a density of the powder.

In the alternating current impedance method, the impedance of a sample is measured by applying an alternating current or an alternating voltage to the sample. In the present invention, a powder is used as the sample, and the impedance characteristics of the powder are obtained a function in which a pressure applied to powder or a density of powder as a variable. For example, desired impedance characteristics are obtained by measuring the impedance of a powder while successively changing the pressure applied to the powder or the density of the powder.

A preferable embodiment of the method for measuring powder properties further includes step B in which information relating to at least one of the components is extracted from the obtained impedance characteristics, the components being a first component that is dependent on the variable and a second component that is not dependent on the variable. The first component that changes along with the variable (a pressure applied to the powder or a density of the powder) includes a lot of information relating to the resistance between the particles of the powder. On the other hand, the second component that is not dependent on the variable includes a lot of information relating to the resistance inside the particles of the powder. For example, the impedance characteristics can be separated into a first component that is dependent on the variable and a second component that is not dependent on the variable by using a complex impedance plot.

In this way, information relating to the resistance between the particles of the powder can be obtained from the first component, and information relating to the resistance inside the particles of the powder can be obtained from the second component. Therefore, a preferable embodiment of the method for measuring powder properties further includes at least one of step C in which information relating to the resistance between the particles of the powder is obtained from the first component, and step D in which information relating to the resistance inside the particles of the powder is obtained from the second component.

Step A includes, for example, changing the frequency of the alternating current or the alternating voltage while fixing the variable (a pressure applied to the powder or a density of the powder) at a predetermined value Xn, and obtaining relationships between the frequency and the impedance of powder at predetermined value Xn. In this case, a complex impedance can be plotted against a predetermined value Xn. By changing Xn, a plurality of complex impedances can be plotted, and the changes in the first component can be tracked.

The frequency of the alternating current or the alternating voltage can be fixed without changing. That is, step A may also include successively changing the variable (a pressure applied to the powder or a density of the powder) while fixing the frequency of the alternating current or the alternating voltage at a predetermined value Ym, and obtaining relationships between the variable and the impedance of the powder at a predetermined value Ym. In this case, by changing Ym, a plurality of complex impedances can be plotted. Therefore, by changing Ym, the changes in the first component can be tracked.

The variable (a pressure applied to the powder or a density of the powder) can be changed by any method, but an efficient method is to apply a pressure to the powder in one direction in a space surrounded by a conductive material, and successively increase the pressure.

In the following, each step is described in detail.

(i) Step A

In step A, an alternating current or an alternating voltage is applied to powder while successively changing the pressure applied to the powder or the density of powder. This allows the impedance characteristics of the powder corresponding to a plurality of different pressures or densities to be obtained.

For example, the frequency of the alternating current or the alternating voltage is changed while fixing the pressure applied to the powder or the density of the powder to X1, and the relationships between the frequency and the impedance of the powder at X1 are obtained. Next, the frequency of the alternating current or the alternating voltage is changed while fixing the pressure applied to the powder or the density of the powder to, for example, X2 (X1<X2), and the relationships between the frequency and the impedance of the powder are obtained. Furthermore, the frequency of the alternating current or the alternating voltage is changed while fixing the pressure applied to the powder or the density of the powder to, for example, X3 (X2<X3), and the relationships between the frequency and the impedance of the powder are obtained. A plurality of impedance characteristics are obtained by repeating such operations, and a plurality of complex impedances can be plotted.

By thus obtaining the plurality of impedance characteristics, a plurality of complex impedances can be plotted for a sample powder, improving measurement accuracy. Also, the first component that is dependent on the pressure applied to the powder or the density of the powder, and the second component that is not dependent on the pressure applied to the powder or the density of the powder can be separated easily and accurately.

Particularly, the accuracy of measurements of powder properties greatly improves when the impedance is measured sequentially by changing the pressure applied to the powder or the density of the powder.

The pressure applied to the powder or the density of the powder can be changed by any method. For example, powder is placed in a space surrounded by a conductive material and a pressure is applied from one direction to the powder. At that time, the pressure is successively increased or successively decreased. The pressure to be applied to the powder may be changed in the range of, for example, 0 to 200 MPa, although it depends on the hardness of the powder. When the pressure is applied to the powder by pressing the powder with a pressing apparatus, the degree of pressure and the density of the powder can be controlled by changing the position of the portion of the pressing apparatus contacting the powder.

The frequency of the alternating current or the alternating voltage may be fixed without changing. For example, the pressure applied to the powder or the density of the powder is changed while fixing the frequency of the alternating current or the alternating voltage to Y1, and the relationships between the pressure or the density and the impedance of the powder at Y1 are obtained. Next, the pressure applied to the powder or the density of the powder is changed while fixing the frequency of the alternating current or the alternating voltage to Y2 (Y1<Y2), and the relationships between the pressure or the density and the impedance of powder are obtained. Furthermore, the pressure applied to the powder or the density of the powder is changed while fixing the frequency of the alternating current or the alternating voltage to Y3 (Y2<Y3), and the relationships between the pressure or the density and the impedance of the powder are obtained. A plurality of impedance characteristics are obtained by repeating such operations.

(ii) Step B

The impedance characteristics include a first component that is dependent on the variable (a pressure applied to the powder or a density of the powder), and a second component that is not dependent on the variable. However, it is difficult to separate the first component from the second component with high accuracy using only a single complex impedance plot. The first component and the second component can be separated with high accuracy using a plurality of complex impedance plots.

The complex impedance plot illustrates the relationships between a frequency of the alternating current or the alternating voltage, and the real part and the imaginary part of the impedance. Generally, the impedance is plotted on a complex plane (Gaussian plane), in which the horizontal axis is used for real part Z', and the vertical axis is used for imaginary part Z". The frequency of the alternating current or the alternating voltage is changed and the impedance at each frequency is plotted on the complex plane. A plurality of substantially semicircular plots are illustrated in a complex impedance plot.

FIG. 1 illustrates an example of the complex impedance plot. The complex impedance plot shown in FIG. 1 includes the first component (region A) that is dependent on a variable (a pressure applied to the powder or a density of the powder), and the second component (region B) that is not dependent on the variable.

In step B, the first component that easily changes depending on the variable is separated highly accurately from the second component that is not dependent on the variable and hardly changes in the plurality of complex impedance plots.

FIG. 2 (a) to FIG. 2 (e) illustrate an example of the complex impedance plots in which the variable is changed from X1 to X5. FIG. 2 (a) illustrates a complex impedance plot with the smallest variable (X1), and FIG. 2 (e) illustrates a complex impedance plot with the largest variable (X5). The first component that is dependent on the variable easily changes due to the pressure applied to the powder or the density of powder, as shown in FIG. 2 (a) to FIG. 2 (e). Thus, the accuracy of the measurement of powder properties decreases if the first component cannot be separated.

On the other hand, the second component that is not dependent on the variable hardly changes due to the pressure applied to the powder or the density of powder, as shown in FIG. 2 (a) to FIG. 2 (e). The second component reflects the resistance inside the particles, and shows characteristics unique to the substance.

(iii) Step C and Step D

In the complex impedance plots shown in FIG. 2 (a) to FIG. 2 (e), the first component is plotted at the high resistance side of the real part, and the second component is plotted at the low resistance side of the real part. The diameter of the semicircle illustrated by the first component plots changes along with the variable (a pressure applied to the powder or a density of the powder). Also, the diameter of the semicircle illustrated by the first component plots corresponds to the interface resistance between the particles of powder. On the other hand, the diameter of the semicircle illustrated by the second component plots corresponds to the resistance inside the particles (bulk).

Figure 3:
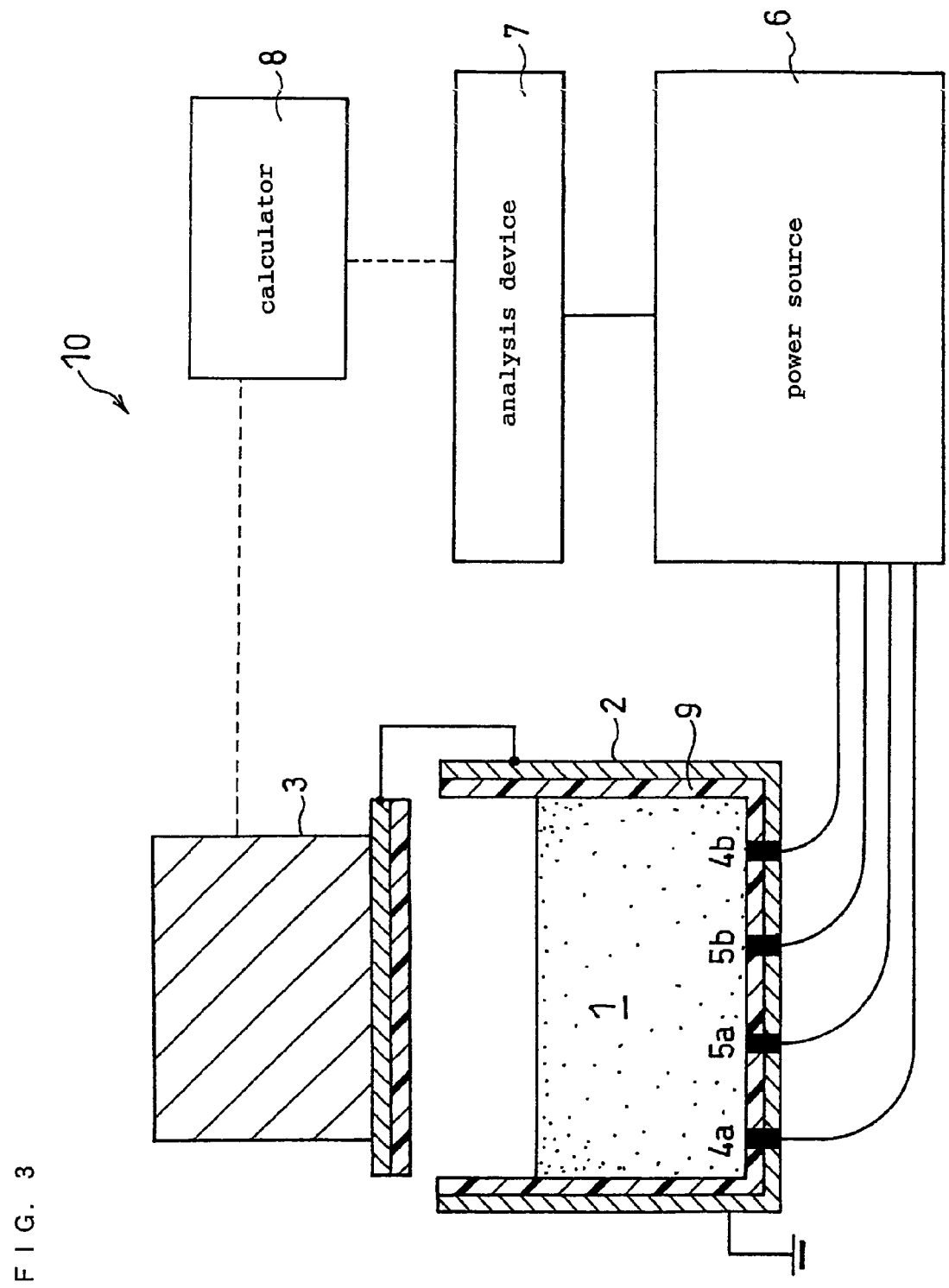
FIG. 3 is a schematic diagram illustrating an embodiment of a device for measuring powder properties.

A device for measuring powder properties is described next with reference to the figures. FIG. 3 is a schematic diagram illustrating an embodiment of the device for measuring powder properties.

A device 10 uses the principle of what is called a four probe method. The device 10 includes a measurement container 2 in which powder 1 is placed, a pressing apparatus that applies a pressure to the powder 1, a pair of current terminals 4a and 4b, a pair of voltage terminals 5a and 5b, an alternating current power source 6, an analysis device 7, and a calculator 8 that calculates the impedance. The pair of current terminals 4a and 4b, and the pair of voltage terminals 5a and 5b correspond to the four probes.

The measurement container 2 forms a space surrounded by a conductive material. The powder 1 is packed into the space at the time of measurement. The conductive material is grounded, and electromagnetically shields the internal portion of the measurement container 2 from the outside. The material of the measurement container 2 is not particularly limited, and includes, for example, stainless steel, iron, aluminum, and the like. The portion of the measurement container 2 to be brought into contact with the powder 1 is preferably made of an insulator 9 with a small dissipation factor, except for the portion where the terminals are connected. Particularly, for example, alumina and the like are preferable. The preferable range of the dissipation factor of the insulator 9 is, for example, 0.002 to 0.02. The shape of the measurement container 2 is preferably columnar, and the bottom area thereof is, for example, 1 to 10 cm$^2$, but not limited thereto. Although the capacity of the space for placing the powder 1 is not limited as well, the capacity may be, for example, 1 to 20 cm$^3$. The shape of the bottom face of the measurement container 2 is not particularly limited. For example, the shape of the bottom face may be rectangular, polygonal, circular, and the like.

The pressing apparatus 3 presses the powder 1 packed in the measurement container 2. Hereinafter, in the pressing apparatus 3, the face that is brought into contact with the powder 1 is referred to as a main face of the pressing apparatus 3. At the time of measurement, the powder 1 is surrounded by the inner walls of the measurement container 2 and the main face of the pressing apparatus 3.

By appropriately selecting the bottom area of the measurement container 2 and the pressing force of the pressing apparatus 3, the volume of the powder 1 surrounded by the measurement container 2 and the main face of the pressing apparatus 3 can be regulated. In order to regulate the volume of the powder 1 surrounded by the measurement container 2 and the main face of the pressing apparatus 3 more precisely, it is preferable that the main face of the pressing apparatus 3 is substantially flat. Similarly, in order to regulate the volume of the powder 1 more precisely, it is preferable that the bottom face of the measurement container 2 and the main face of the pressing apparatus 3 are substantially parallel. The accuracy of the measurement of the powder properties thus improves further. The material of the pressing apparatus 3 is not particularly limited, and, for example, stainless steel and the like may be used. The main face of the pressing apparatus 3 is preferably made of an insulator with a small dissipation factor. To be specific, for example, alumina and the like may be used. The preferable range of the dissipation factor in the main face of the pressing apparatus 3 is, for example, 0.002 to 0.02.

The shape of the main face of the pressing apparatus 3 is not particularly limited, as long as the powder 1 packed in the measurement container 2 can be pressed. For example, the shape of the main face may be rectangular, polygonal, circular, and the like. It is preferable that the shape of the main face of the pressing apparatus 3 is substantially the same as the shape of the bottom face of the measurement container 2.

Although the bottom face of the measurement container 2 and the main face of the pressing apparatus 3 are disposed so that they are substantially parallel in the vertical direction (up and down) in FIG. 3, the disposition is not limited thereto, and the bottom face of the measurement container 2 and the main face of the pressing apparatus 3 may be disposed so as to be parallel, for example, in the horizontal direction or in an oblique direction.

A pressure control device (not shown) that controls the pressure to be applied to the powder 1 so that the pressure successively changes may be added to the pressing apparatus 3. The pressure control device controls the movement and stoppage of the pressing apparatus 3. However, such a control device is not absolutely necessary, and the pressure may be appropriately adjusted manually.

The pair of current terminals 4a and 4b, and the pair of voltage terminals 5a and 5b are exposed inside the measurement container 2. All of these terminals are preferably disposed at the bottom face of the measurement container 2. In order to reduce the contact resistance between the terminals and the powder 1, each terminal is preferably gold-plated at the area where the powder 1 comes into contact. The materials of the current terminals and the voltage terminals are not particularly limited as well. For example, metals such as stainless steel, platinum, gold, titanium, and nickel, and alloys thereof may be used.

The power source 6 applies an alternating current of an arbitrary frequency to the pair of current terminals 4a and 4b, or an alternating voltage of an arbitrary frequency to the pair of voltage terminals 5a and 5b while the powder 1 is pressed by the pressing apparatus 3. The frequency of the alternating current or the alternating voltage is not particularly limited. For example, the frequency of the alternating current or the alternating voltage is 100 MHz to 1 mHz, and preferably 10 MHz to 10 mHz. The power source 6 is not particularly limited, and, for example, a potentiostat and the like may be used.

The analysis device 7 measures a voltage generated between the pair of voltage terminals 5a and 5b by the application of an alternating current, or an electric current generated between the pair of current terminals 4a and 4b by the application of an alternating voltage. For example, when an alternating current is applied to the pair of current terminals 4a and 4b, a voltage is generated between the pair of voltage terminals 5a and 5b. By measuring the voltage at this time, the impedance of the powder can be obtained from the current value and the voltage value. To be specific, for example, an FRA (Frequency Response Analyzer) may be used as the analysis device 7.

The impedance of the powder 1 can be obtained from the current value and the voltage value using a general computer.

Although the duration of the application of the alternating current or the alternating voltage is not particularly limited, the duration is preferably 1 to 60 minutes, and more preferably 1 to 15 minutes, per single complex impedance plot. When the duration of the application of the alternating current or the voltage is long, the temperature of the powder 1 may rise. This may cause a decline in measurement accuracy and, therefore, the temperature of the powder 1 is preferably controlled so as to be substantially constant (for example, 20 to 25° C.). The method for controlling the temperature of the powder 1 is not limited. For example, the measurement container 2 may be disposed in a constant temperature bath, or a Peltier element may be disposed in the measurement container 2.

A characteristic impedance of the pair of current terminals 4a and 4b, a characteristic impedance of the pair of voltage terminals 5a and 5b, and a characteristic impedance of the power source 6 are preferably matched. The matching method is not particularly limited, and for example, characteristic impedances are matched by using current terminals or voltage terminals having a coaxial structure, and connecting the current terminal. the voltage terminal, and the power source with a coaxial cable. The value of the characteristic impedance is not particularly limited, and may be matched at, for example, 50Ω.

The characteristic impedance of a connecting means that connects the power source 6, the pair of current terminals 4a and 4b, and the pair of voltage terminals 5a and 5b preferably matches the characteristic impedance of the pair of current terminals 4a and 4b, the characteristic impedance of the pair of voltage terminals 5a and 5b, and the characteristic impedance of the power source 6. For the connecting means, for example, a coaxial cable is preferably used, and the length of the coaxial cable is, for example, preferably 30 cm or less. For the portion connecting the connecting means and the pair of current terminals 4a and 4b, and the pair of voltage terminals 5a and 5b, a coaxial connector such as an SMA connector or an N-type connector is preferably used.

The calculator 8 may further include a function of controlling the power source 6 and the pressing apparatus 3. The calculator 8 is preferably electrically connected to the power source 6 and the pressing apparatus 3, and information can be exchanged between each. To be specific, the calculator 8 controls, for example, the activation and termination of the power source 6 and the activation and termination of the pressing apparatus 3.

Furthermore, it is preferable that information relating to the calculated impedance characteristics can be shown on a display and the like.

For example, the calculator 8 preferably includes a processing circuit realized by a microcomputer including a CPU (central processing unit), a memory, and the like; and a display for showing the computation result that is computed by the processing circuit. For the memory, those commonly used in the art may be used, including, for example, a read only memory (ROM), a random access memory (RAM), and a hard disk drive (HDD).

The computation in the processing circuit includes, for example, calculation of the impedance characteristics of the powder 1 based on a voltage generated between the pair of voltage terminals 5a and 5b by the application of an alternating current. For the display, a liquid crystal display, a plasma display, or the like may be used.

The measurement of the properties of the powder 1 is carried out, for example, as described below.

First, the powder 1 is packed in the measurement container 2. Afterwards, the powder 1 is pressed by the pressing apparatus 3, and a predetermined pressure is applied to the powder 1. thereby adjusting the density of the powder 1.

Next, the power source 6 (potentiostat) and the analysis device 7 (FRA) are activated, and an alternating current is applied to the pair of current terminals 4a and 4b. The alternating current applied to the pair of current terminals 4a and 4b is inputted to the calculator 8 from the FRA. Then, the FRA measures the voltage generated between the pair of voltage terminals 5a and 5b, and inputs the result to the calculator 8. The calculator 8 calculates the impedance characteristics of the powder 1 from the values inputted.

Afterwards, a plurality of different predetermined pressures are applied to the powder 1, and a plurality of the impedance characteristics of the powder 1 are calculated in the same manner. The calculator 8 calculates the first component and the second component from the obtained information on the plurality of impedance characteristics, and shows the result on the display.

Figure 4:
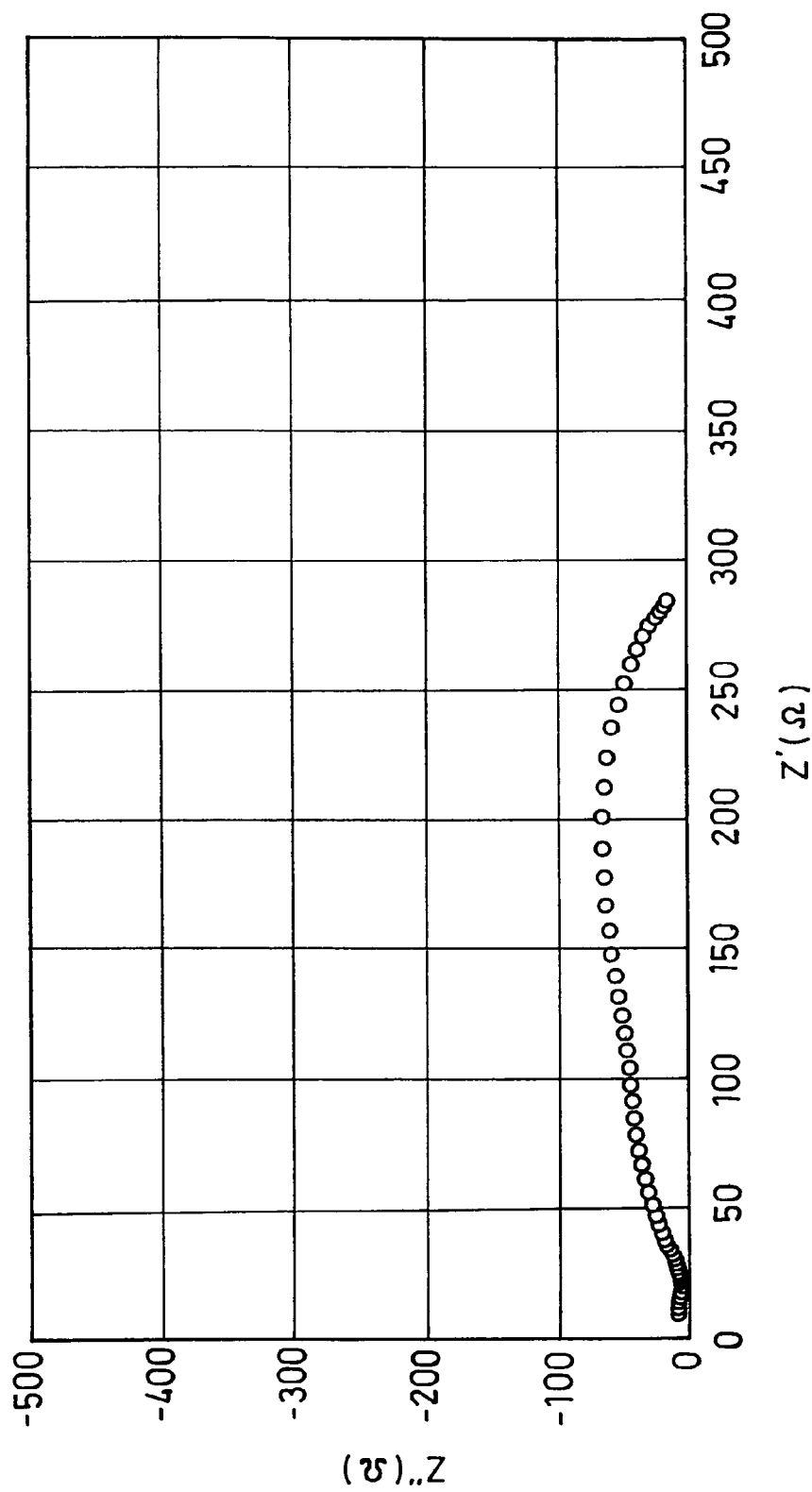
FIG. 4 is a complex impedance plot illustrating the impedance characteristics of a lithium manganate powder.

A complex impedance plot of lithium manganate powder (average particle size 20 μm) is shown in FIG. 4 as one embodiment of the present invention. In the measurement of the powder properties shown in FIG. 4, 3 g of lithium manganate powder is used. The capacity of the space that holds the powder is set to 7 cm$^3$, and the pressure applied to the powder is set to 100 MPa. That is, the density of the lithium manganate powder at the time of the measurement is set to 2.8 g/cm$^3$. The measurement is carried out while changing the frequency from 10 MHz to 1 Hz.

Although the invention has been described in terms of the presently preferred embodiments, it is to be understood that such disclosure is not to be interpreted as limiting. Various alterations and modifications will no doubt become apparent to those skilled in the art to which the invention pertains, after having read the above disclosure. Accordingly, it is intended that the appended claims be interpreted as covering all alterations and modifications as fall within the true spirit and scope of the invention.

The invention claimed is:

1. A method for measuring powder properties, the method comprising:
    step A in which impedance characteristics of a powder are obtained by applying to the powder, an alternating current of a predetermined frequency range or an alternating voltage of a predetermined frequency range, the impedance characteristics being represented by a function which has as a variable, pressure applied to the powder or density of the powder; and
    step B in which information related to at least one of a first component dependent on the variable and a second component not dependent on the variable, is extracted from the impedance characteristics obtained.

2. The method for measuring powder properties in accordance with claim 1, further comprising at least one of step C in which information relating to resistance between the particles of the powder is obtained from the first component, and step D in which information relating to resistance inside the particles of the powder is obtained from the second component.

3. The method for measuring powder properties in accordance with claim 1, wherein said step A comprises changing the frequency of an alternating current or an alternating voltage while fixing the variable to a predetermined value Xn, and obtaining relationships between the frequency and the impedance of the powder at the predetermined value Xn.

4. The method for measuring powder properties in accordance with claim 1, wherein said step A comprises successively changing the variable while fixing the frequency of the alternating current or the alternating voltage at a predetermined value Ym, and obtaining relationships between the variable and the impedance of the powder at the predetermined value Ym.

5. The method for measuring powder properties in accordance with claim 1, wherein the variable is changed by applying a pressure to the powder in one direction in a space surrounded by a conductive material, and successively increasing the pressure.

6. A device for measuring powder properties comprising:
    a measurement container forming a space surrounded by a conductive material that is grounded;
    a pressing apparatus that presses powder packed in the measurement container;
    a pair of current terminals and a pair of voltage terminals that are exposed inside the measurement container;
    a power source that applies an alternating current of an arbitrary frequency to the pair of current terminals, or an alternating voltage of an arbitrary frequency to the pair of voltage terminals, while the pressing apparatus is applying a pressure to the powder;
    an analysis device that analyzes a voltage generated between the pair of voltage terminals by the application of the alternating current, or a current generated between the pair of current terminals by the application of the alternating voltage; and
    a calculator that obtains impedance characteristics of the powder by calculating the impedance of the powder from the voltage generated between the pair of voltage terminals or from the current generated between the pair of current terminals,
    wherein the impedance characteristics are represented by a function which has as a variable, pressure applied to the powder or density of the powder, and
    the calculator extracts information related to at least one of a first component dependent on the variable and a second component not dependent on the variable, from the impedance characteristics obtained.

* * * * *